United States Patent
Von Marcard et al.

(10) Patent No.: US 10,638,958 B2
(45) Date of Patent: May 5, 2020

(54) DEVICE AND METHOD FOR DETERMINING RELATIVE DISPLACEMENTS OF BODY PARTS OR BODY AREAS

(71) Applicant: OTTO BOCK HEALTHCARE GMBH, Duderstadt (DE)

(72) Inventors: Timo Von Marcard, Hannover (DE); Jorg Krukenberg, Duderstadt (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 68 days.

(21) Appl. No.: 14/410,502

(22) PCT Filed: Jun. 21, 2013

(86) PCT No.: PCT/EP2013/001845
§ 371 (c)(1),
(2) Date: Dec. 22, 2014

(87) PCT Pub. No.: WO2014/000876
PCT Pub. Date: Jan. 3, 2014

(65) Prior Publication Data
US 2015/0366489 A1   Dec. 24, 2015

(30) Foreign Application Priority Data
Jun. 27, 2012 (DE) ........................ 10 2012 012 695

(51) Int. Cl.
*A61B 5/00* (2006.01)
*A61B 5/11* (2006.01)
(Continued)

(52) U.S. Cl.
CPC .......... *A61B 5/1127* (2013.01); *A61B 5/0059* (2013.01); *A61B 5/05* (2013.01);
(Continued)

(58) Field of Classification Search
CPC .... A61B 2090/3945; A61B 2090/3958; A61B 2090/3975; A61B 2562/164;
(Continued)

(56) References Cited

U.S. PATENT DOCUMENTS 3,881,468 A * 5/1975 Foltz .................. A61B 1/00032
362/804
4,555,625 A    11/1985 Mosier et al.
(Continued)

FOREIGN PATENT DOCUMENTS

CN    101650433 A    2/2010
CN    101655553 A    2/2010
(Continued)

OTHER PUBLICATIONS

PCT International Search Report for PCT International Patent Application No. PCT/EP2013/001845, mailed Sep. 24, 2013.

*Primary Examiner* — Mark D Remaly
(74) *Attorney, Agent, or Firm* — Holland & Hart, LLP

(57) ABSTRACT

Devices and methods for determining relative displacements of body parts or body areas, with a transmitter and a sensor associated with the transmitter, wherein at least one shadowing device, which is displaceable relative to the sensor and/or the transmitter and is fixed to at least one body part or body area, is arranged between the transmitter and the sensor.

14 Claims, 5 Drawing Sheets

(51) Int. Cl.
  *A61B 90/00* (2016.01)
  *G01D 5/34* (2006.01)
  *A61B 5/05* (2006.01)

(52) U.S. Cl.
  CPC ............ *A61B 5/1114* (2013.01); *A61B 90/39* (2016.02); *G01D 5/34* (2013.01); *A61B 2090/3945* (2016.02); *A61B 2090/3958* (2016.02); *A61B 2090/3975* (2016.02); *A61B 2562/164* (2013.01)

(58) Field of Classification Search
  CPC ....... A61B 5/0059; A61B 5/05; A61B 5/1114; A61B 5/1127; A61B 90/39; G01D 5/34
  See application file for complete search history.

(56) References Cited

U.S. PATENT DOCUMENTS

| | | | |
|---|---|---|---|
| 5,376,785 A | 12/1994 | Chin et al. | |
| 8,241,231 B2 | 8/2012 | Bausewein et al. | |
| 2002/0016533 A1* | 2/2002 | Marchitto | A61B 5/0066 600/310 |
| 2007/0177162 A1 | 8/2007 | Glueck | |
| 2009/0220415 A1* | 9/2009 | Shachaf | A61B 5/0071 424/1.11 |
| 2011/0316527 A1 | 12/2011 | Dolsak et al. | |

FOREIGN PATENT DOCUMENTS

| | | |
|---|---|---|
| DE | 1808485 U | 3/1960 |
| DE | 19632273 A1 | 2/1998 |
| DE | 102004013683 A1 | 11/2005 |
| DE | 102006045138 A1 | 11/2007 |
| DE | 102009005536 A1 | 9/2010 |
| FR | 2954493 A1 | 6/2011 |
| GB | 1498409 | 1/1978 |
| WO | 9807086 A1 | 2/1998 |

\* cited by examiner

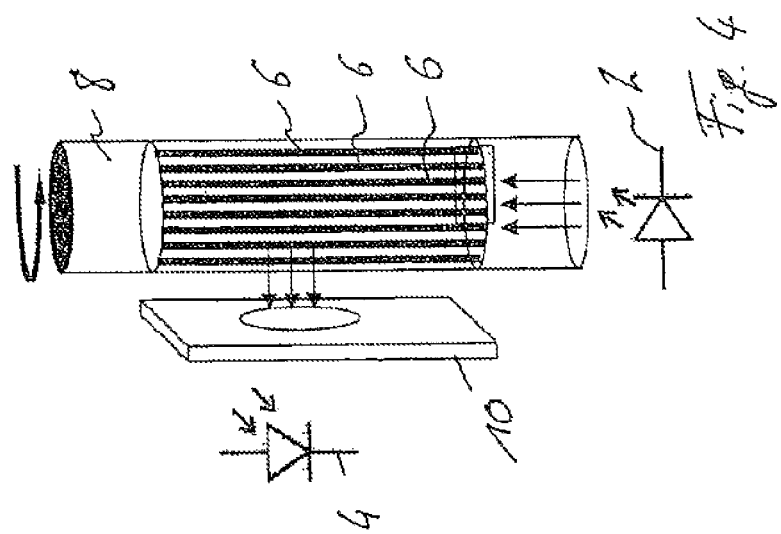
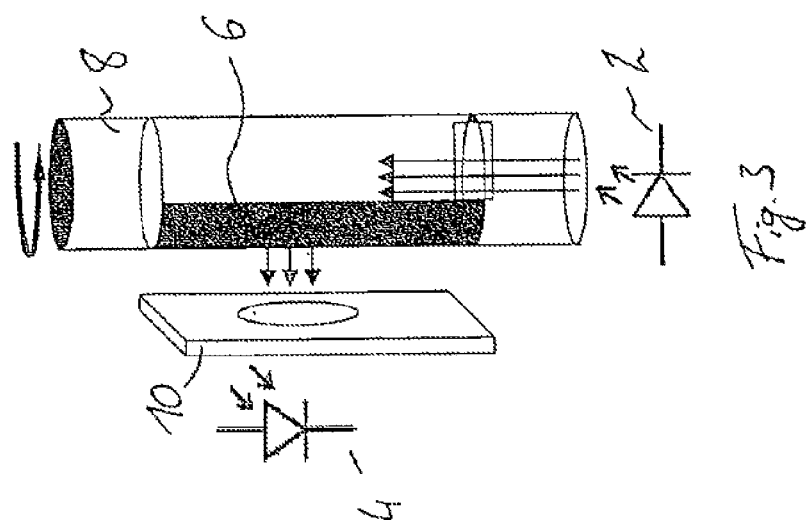

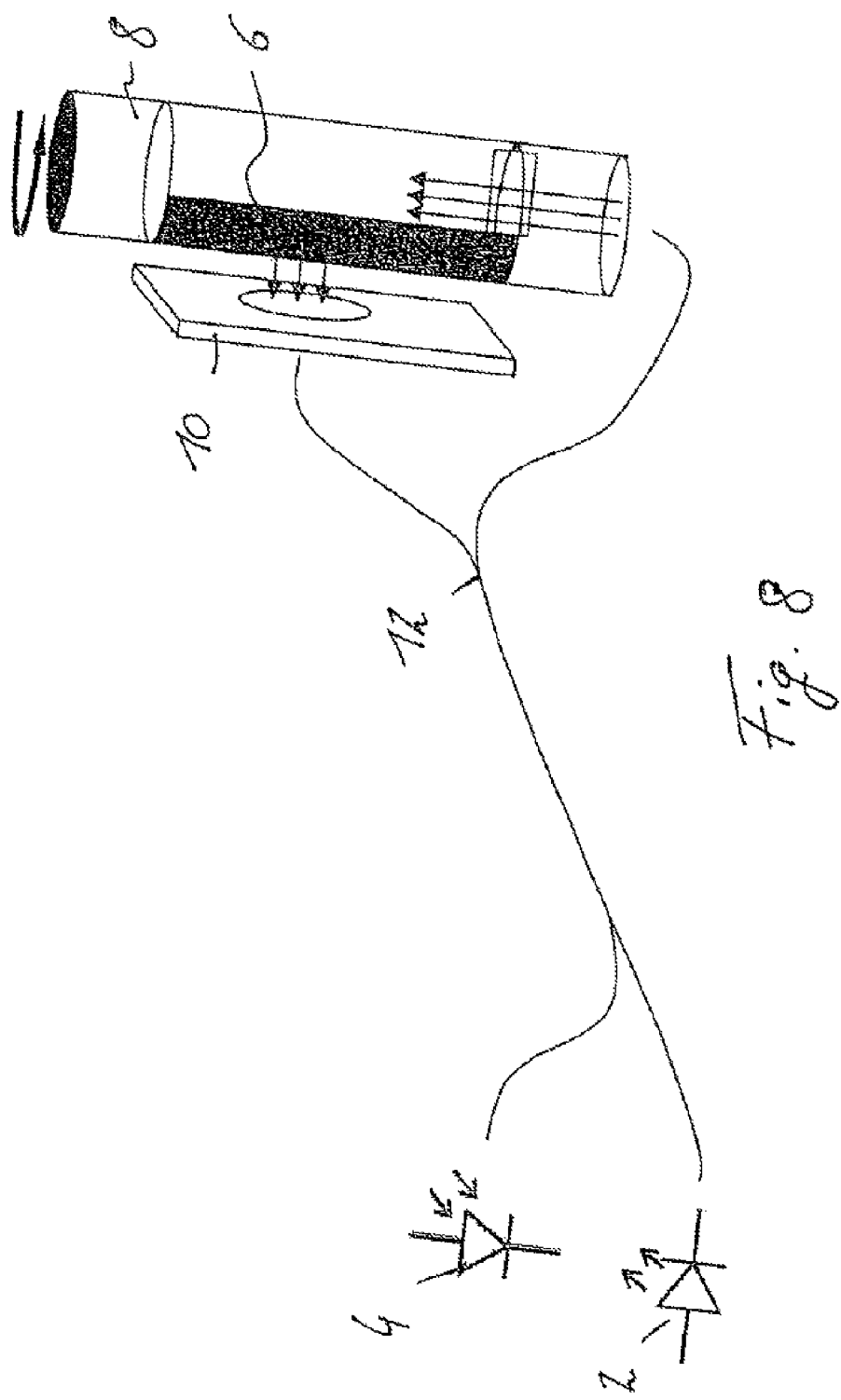

DEVICE AND METHOD FOR DETERMINING RELATIVE DISPLACEMENTS OF BODY PARTS OR BODY AREAS

TECHNICAL FIELD

The invention relates to a device and a method for determining relative displacements of body parts or body areas, comprising a transmitter and a sensor assigned to the transmitter. The invention is suitable, in particular, for registering the spinal torsion or spinal rotation during the movement.

BACKGROUND

In order to register movement data and movement sequences, a method in which markers are attached to the body surface of a person is known in addition to pure image recording by means of one or more cameras. The moving person is recorded by a camera, with the markers being arranged at the fulcrums. The movements of the fulcrums in relation to one another are converted as a model in a computer following the registration by the camera apparatuses and imaged on a screen. Relative movements of body parts or body areas in relation to one another can be calculated from the model, wherein the calculation is based on model assumptions. Thus, the spinal column is usually assumed to be a rod, on which the pelvis and the shoulders are secured.

The latter method requires high instrument outlay, is generally only applicable in a specific surroundings situation and allows no, or only inaccurate, conclusions to be drawn about the actual twist within the spinal column or the actual displacement of individual body areas or body parts in relation to one another.

Document 10 2009 005 536 A1 relates to a rotational angle sensor for contactlessly determining the rotational angle of a rotational axis, comprising an optical radiation source and a detector, wherein a shadowing structure on a disk is arranged in the beam path between the radiation source and the detector, the position of which shadowing structure changes with the rotational axis. The shadowing structure is at least partly illuminated by the radiation from the radiation source, depending on the rotational angle of the rotational axis, and imaged on the detector. This allows measurement errors to be avoided or reduced and the rotational angle, to be registered, of the rotational axis to be established more precisely.

SUMMARY

An object of the present invention is to provide a device and a method by means of which direct measurement value registration is possible in a cost-effective and reliable way.

According to the invention, this object is achieved by a device comprising the features of the main claim and by a method comprising the features of the coordinate claim. Advantageous embodiments and developments of the invention are disclosed in the dependent claims, the description and in the figures.

The device for determining relative displacements of body parts or body areas, comprising a transmitter and a sensor assigned to the transmitter, provides for at least one shadowing apparatus which is secured to at least one body part or body area and which is displaceable relative to the sensor and/or the transmitter to be arranged between the transmitter and the sensor. The sensor and/or the transmitter are embodied in a manner securable to the body. By securing the shadowing apparatus on a body part or a body area, it is possible to determine a relative movement in this body area or between two body parts in a simple manner and with a high accuracy and spatial resolution. Thus, in particular, it is possible to detect a twist of the spinal column over the whole length thereof by securing the shadowing apparatus at one end and by arranging the sensor at the other end of the spinal column. As a result of the freely selectable positioning of the sensor along the shadowing apparatus, it is likewise possible to obtain precise securing of the measuring point, and so forming a model is no longer necessary for determining the relative displacement. The directed emission of signals, e.g. light, radiation, electromagnetic waves or magnetic patterns, in one direction is also understood to be a shadowing apparatus, and so, for example, a light source emitting only in one direction emits no, or only little, light on the side facing away from the emission direction; this has the same effect as if a light source scattering to all sides is darkened in regions by a stop or the like. An analogous statement applies to alternative signal forms in which no light waves are used.

The shadowing apparatus can be arranged between the sensor and the transmitter directed to the sensor. This is the case, in particular, when the transmitter or the emergence point of the transmitter lies opposite to the sensor and the shadowing apparatus is arranged between the transmitter or emergence point of the transmitter and the sensor. Thus, the shadowing apparatus is transmitted through, penetrated, transilluminated or illuminated in the direction of the sensor, as a result of which it is possible to direct a high signal intensity in the direction of the sensor.

A variant of the invention provides for the transmitter to be embodied as a light source, magnet, emitter or transmitter emitting electromagnetic waves. Here, the transmitter is embodied in a manner corresponding to the sensor and it transmits signals or a signal that can be registered by the sensor. Here, the signal can be emitted in a manner directed directly in the direction of the sensor or it can be guided by a conductor or several conductors in the direction of the sensor and aligned with the latter.

It is possible for a plurality of shadowing apparatuses to be arranged in succession in the displacement direction of the shadowing apparatus. If provision is predominantly made for twisting of the shadowing apparatus, a plurality of shadowing apparatuses can be arranged in the rotational direction around the circumference of e.g. a main body. If a change in length or bending accompanying a change in length is to be measured, a plurality of shadowing apparatuses can, in the longitudinal extent, be arranged in succession along the displacement direction.

The shadowing apparatus can be embodied as a coating applied to a main body or as a region of the main body with deviating signal transmittance, e.g. light transmittance or light emission. In principle, it is also possible for the shadowing apparatus to consist of an element which is impermeable to the signal medium, e.g. opaque to light, and does not have a rotationally symmetrical structure or has flattenings or contour patterns, by means of which it is possible to detect a relative displacement. In the case of a flattening, the detection emerges as a result of the increased or reduced shadowing of the sensor during twisting; in the case of a displacement, contouring in the form of a pattern, for example as a result of projections in the longitudinal extent on the outer side, is a possible indicator for relative displacement. To the extent that the shadowing apparatus is transirradiated or transilluminated, e.g. coatings, which are advantageously applied on the outer side, are possible and provided on a radiation-transmissive or light-transmissive main body. These coatings can be arranged in strip form in a longitudinal direction or in a circumferential direction in order to vary the incidence rate on the sensor in the case of a rotation or a longitudinal displacement. It is likewise possible for at least one region of the main body to be embodied with a deviating signal transmittance or signal emission, i.e., for example, to bring about scattering or absorption of the incident or passed signal, e.g. light, by roughening or by modifying the refractive index such that different signal intensities are incident on the sensor depending on the position of the main body. It is likewise possible and provided for the shadowing apparatus to be embodied as a filter, e.g. a polarization filter. The degree of transmission is modified by the relative displacement of the filter, leading to different intensities on the sensor. The transmitter advantageously emits polarized light in order to amplify the effect. The shadowing region can also be embodied as a region with a deviating magnetic flux, a deviating field line alignment or field line density such that a change in position can be detected by means of a magnetosensitive sensor.

The main body can have a substantially round cross section, which is advantageous for establishing twists, in particular torsion of a spinal column, particularly in the case of shadowing devices in the form of coatings or strip patterns. The main body can have a flexible embodiment such that it can follow the multifaceted movement possibilities of the body and so that a multiplicity of measurement points can be serviced by only one main body. If the main body has an elongate embodiment and the signal, e.g. light, falls perpendicular to the longitudinal extent of the main body in the direction of the sensor, the main body is penetrated, transilluminated or light is guided out of the light-conducting main body in the direction of the sensor. In the case of a round cross section of the main body, the main body with the shadowing apparatus is embodied as a rotational shaft which itself effects an optical stop or shadowing, as a result of which a very small and cost-effective design can be achieved. A corresponding statement applies to a non-light-transmissive main body with a non-rotationally symmetric cross-section or a pattern in the contour extending in the longitudinal direction.

A plurality of measurement points on a shadowing apparatus may be possible around or along a longitudinal axis of the shadowing apparatus, which in turn can be embodied with any desired flexibility, wherein merely sufficient torsion stiffness must be ensured in order to be able to detect a twist of the body on which the main body is secured. In the case of a length measurement, there advantageously is no changeability in length; this can be achieved in the case of a flexible main body by e.g. working in a flexible but non-elastic element, for example a high-strength fiber material. In order to establish the twist, it is advantageous if the shadowing apparatus is securable to a body part or body area in a torsion resistant manner at one end and freely rotatable at the other end. In addition to the free rotatability, displaceability relative to the sensor apparatus can also be provided at the other end such that a length change can also be registered. If the transmitter is situated opposite to the sensor, these are advantageously secured in a stationary manner in relation to one another, for example on a carrier apparatus which can be adhered or latched onto clothing or secured in another way; if light emergence occurs in a direction toward the sensor through a main body, on which the shadowing apparatus is arranged or embodied, the rigid assignment of the sensor to a transmitter is dispensed with.

At least one apparatus can be assigned to the shadowing apparatus, on which at least one apparatus, which is to be secured on a body part or body area, at least one sensor is fastened and the shadowing apparatus is mounted in a manner displaceable relative to the sensor. What this ensures is the assignment of the sensor to a specific point on the body and guiding of the shadowing apparatus such that the spatial assignment is maintained apart from one or two degrees of freedom when the shadowing apparatus is displaced. The apparatus for securing on a body part may include guide apparatuses, in which the shadowing apparatus is guided in a twistable and/or displaceable manner. These apparatuses can be embodied as sleeves, envelopes or the like. Arranged on the apparatuses are sensors or pickups for lines which guide the signal to the sensors, and so the twist or displacement can be detected by a relative displacement between the shadowing apparatus and the devices, and hence between the shadowing apparatus and the sensors or the pickups.

The shadowing apparatus can be arranged at, or embodied on, a main body embodied as a signal conductor, wherein the transmitter can be arranged next to the signal conductor and irradiate the latter or it can be assigned to the signal conductor in such a way that the transmitter feeds the signal or the signals in the longitudinal extent of the signal conductor into the latter. As a result of reflection present within the signal conductor, signals, radiation, electromagnetic waves or light can penetrate radially outward from the signal conductor over the whole length of the signal conductor, e.g. optical waveguide. As a result of installing appropriate elements, e.g. optical elements such as mirrors, prisms or the like, it is possible to provide a targeted deflection of the signal in specific regions or directions. If a punctiform or strip-shaped directed beam is deflected in a direction directed radially outward, the remaining circumference of the signal conductor is to be considered to be a shadowing apparatus since less of the signal penetrates to the outside in this region than in the region in which the signal is directed out of the signal conductor. Feeding the signal in the longitudinal extent of the signal conductor is advantageous in that only one transmitter needs to be provided over the whole length of the signal conductor and a plurality of sensors can be arranged along the signal conductor in order to detect the respective displacement.

The sensor is advantageously embodied as an apparatus which measures the signal intensity in one or more frequency ranges of the signal, e.g. light. Just like photodiodes or phototransistors, infrared detectors are likewise provided as sensors. A restriction to the visible light spectrum is not envisaged. A plurality of sensors can be arranged in succession in the longitudinal extent of the shadowing apparatus. An evaluation apparatus can be assigned to the sensor; the former establishes the direction in which, and the extent to which, a relative displacement takes place. In order to avoid stray signals from being registered, a stop can be arranged in front of the sensor and, optionally, in front of the transmitter.

The method for measuring a relative displacement of body parts or body areas in relation to one another provides for a shadowing apparatus to be secured in a stationary manner to a first body part or body area at one point, a signal to be transmitted in the direction of a sensor and the shadowing apparatus to be displaced due to a relative displacement of body parts or body areas. Only changing signal incidence on the sensor due to the displacement of the shadowing apparatus is registered and evaluated in an evaluation apparatus. A different signal emerges for the sensor depending on the change of the signal incidence, and so the corresponding movement is detected depending on the possibility of the relative movement between signal and sensor. If only a rotation is possible, a rotation is detected; if a longitudinal displacement is possible, a corresponding longitudinal displacement is detected. In principle, it is also possible to register a combined displacement by combining a plurality of shadowing apparatuses or sensors. A precondition is that the sensor or a pickup is arranged as stationary as possible on the body part, for example by virtue of being adhered or held at the desired position by a piece of clothing, while the shadowing apparatus is displaceable relative to the sensor or pickup.

The shadowing apparatus can be embodied as an elongate main body, wherein one end of the main body is secured in a torsion resistant manner and at least two sensors arranged offset in relation to one another are arranged next to the shadowing apparatus such that the rotational direction can be determined by evaluating the phase shift of the sensor signals. Therefore, the movement direction is also detected in addition to the scope of the movement. As an alternative to determining the rotational direction, it is also possible to determine both the longitudinal displacement and the displacement direction by arranging two sensors in succession in the displacement direction.

The signal can be fed into a main body, embodied as a signal conductor, along the longitudinal extent thereof and the signal can be decoupled from the signal conductor in the direction of the sensor, wherein at least one shadowing apparatus is arranged at, or embodied on, the signal conductor.

The above-described device serves, in particular, for carrying out the method which is likewise described above. The claimed invention renders it possible, in particular, to perform a measurement of the spinal torsion or rotation by applying or connecting a sensor with a textile piece of clothing. It is likewise possible to register a length change, for example by the deformation of the textile. The design of the invention enables a space-saving and cost-effective solution which is insensitive to most environmental influences. A plurality of measurement points are possible along a shaft, wherein the shaft may have any desired flexibility but not have elasticity in respect of the movement to be measured.

BRIEF DESCRIPTION OF THE DRAWINGS

Below, exemplary embodiments of the invention are explained in more detail on the basis of the attached figures. In detail:

FIG. 3 shows a variant of FIG. 1;
FIG. 4 shows a further variant of FIG. 1;
FIG. 7 shows a device in accordance with FIG. 6 in the twisted state and
FIG. 8 shows a device in accordance with FIG. 3 with optical waveguides to a light source and a sensor.

DETAILED DESCRIPTION

Figure 1:
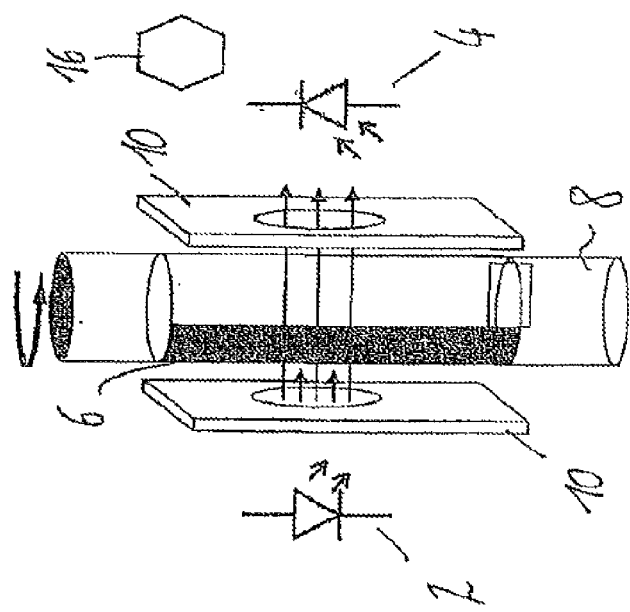
FIG. 1 shows a basic design of a measurement device.

FIG. 1 depicts a schematic illustration of a device for determining relative displacements of body parts and body areas, comprising a light source as a transmitter 2, which transmits light in the direction of the sensor 4 through two stops. The transmitter 2 is embodied as a light-emitting diode (LED). The sensor 4 is embodied as a photodiode. A shadowing apparatus 6, which is fastened to an elongate main body 8, is arranged between the transmitter 2 and the sensor 4. In the depicted exemplary embodiment, the shadowing apparatus 6 is applied as a light-opaque coating on the outer side; alternative shadowing apparatuses are possible. By way of example, the main body 8 made of a light-opaque material comprising a flattening may be arranged on one side of the circumference such that a different radiation intensity is applied to the sensor 4 by twisting the main body 8 about the longitudinal axis thereof. The rotation about the longitudinal axis of the main body 8 is represented by the arrow. Alternating rotational movements can be possible. In the depicted exemplary embodiment, the main body 8 is, as a matter of principle, light-transmissive such that the light from the transmitter 2 can be incident on the sensor 4 in a manner substantially unimpeded by the stops 10, apart from in the region provided with a shadowing device 6. From the sensor 4, the received signal is transmitted to an evaluation apparatus 16, where the signal of light intensity is evaluated.

Figure 2:
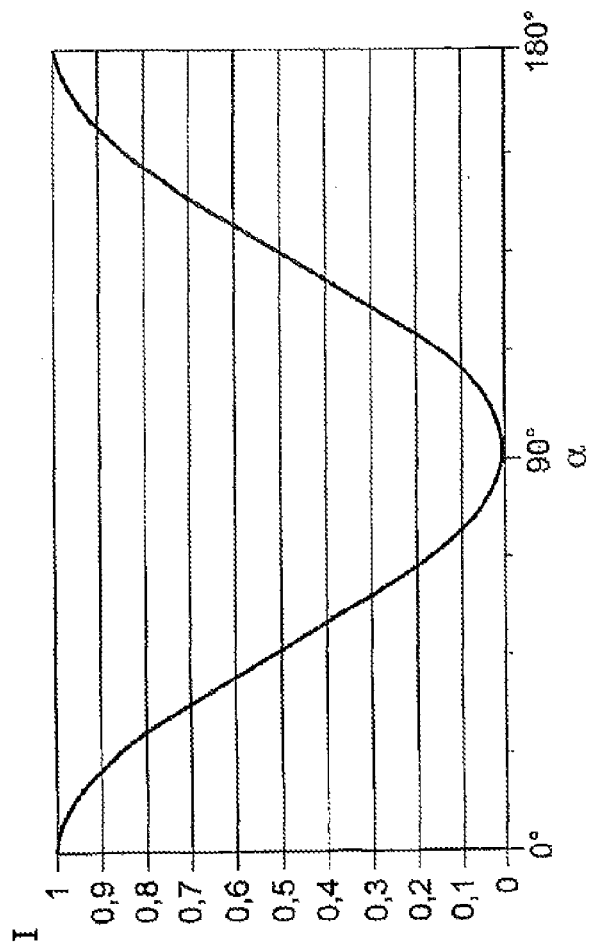
FIG. 2 shows a schematic intensity profile of a measurement signal.

FIG. 2 schematically plots the intensity of the light incidence over the rotational angle $\alpha$. There is a maximum light intensity in an initial position of 0°. When the main body 8, and hence also the shadowing apparatus 6, is twisted, the intensity is increasingly reduced until it is 0 in the case of a twist of 90°, meaning that the stops 10 are completely covered by the shadowing apparatus 6, and so no light from the transmitter 2 reaches the sensor 4. If the shadowing apparatus 6 is twisted further, the light intensity I increases again until it has returned to the intensity maximum at a twist through 180°, where the stops 10 are once again completely cleared. Depending on the size of the stops 10 and the shadowing apparatus 6, the region of complete shadowing may occur over a different rotational range; it may likewise be the case that the shadowing is not complete, and so the sensor 4 continues to detect light when an intensity minimum is reached. It can also be possible for the region of complete shadowing of the stops 10 to occur following a twist through less than 90° such that complete shadowing of the light incidence on the sensor 4 occurs earlier.

A variant of the invention is depicted in FIG. 3, in which the light of the transmitter 2 is fed into the main body in the longitudinal direction thereof instead of there being transillumination of the transmissive main body 8 in the direction of the sensor 4. Therefore, the main body 8 acts as an optical waveguide in which the light propagates in the direction of longitudinal extent. As a result of the reflection on the inner side of the main body 8, some of the light is deflected radially outward, and so light radiation is incident on the sensor 4 through the stops 10. The radially outwardly penetrating radiation is held back by the shadowing apparatus 6, for example a reflecting coating, such that the intensity pattern depicted in FIG. 2 occurs in the case of the main body 8 twisting relative to the sensor 4. In principle, instead of a relatively narrow shadowing apparatus 6, it is also possible for only a relatively narrow light window to be present in the shadowing apparatus 6 in order to cast a light strip onto the sensor 4. A corresponding intensity distribution is also achieved in that case, but at a lower level.

A further variant of the device is shown in FIG. 4, in which a multiplicity of shadowing apparatuses 6 in the form of light-opaque strips are arranged around the circumference of the main body 8. The light is coupled in at a front-face end of the main body 8; decoupling of the light in the direction of the sensor 4 can be increased or caused by optical installations within the main body 8, for example by prisms or reflection apparatuses. As a result of arranging a plurality of shadowing apparatuses 6 in the circumferential direction, that is to say about the longitudinal axis of the main body 8 in the case of rotation, i.e. in succession in the displacement direction, it is possible to easily establish rotational direction and twist, particularly if the shadowing apparatuses 6 are not arranged equidistantly from one another on the main body 8.

If a plurality of sensors 6 are arranged in succession in the displacement direction, it is also possible to establish the rotational direction in addition to the rotational angle by evaluating a phase shift.

Figure 5:
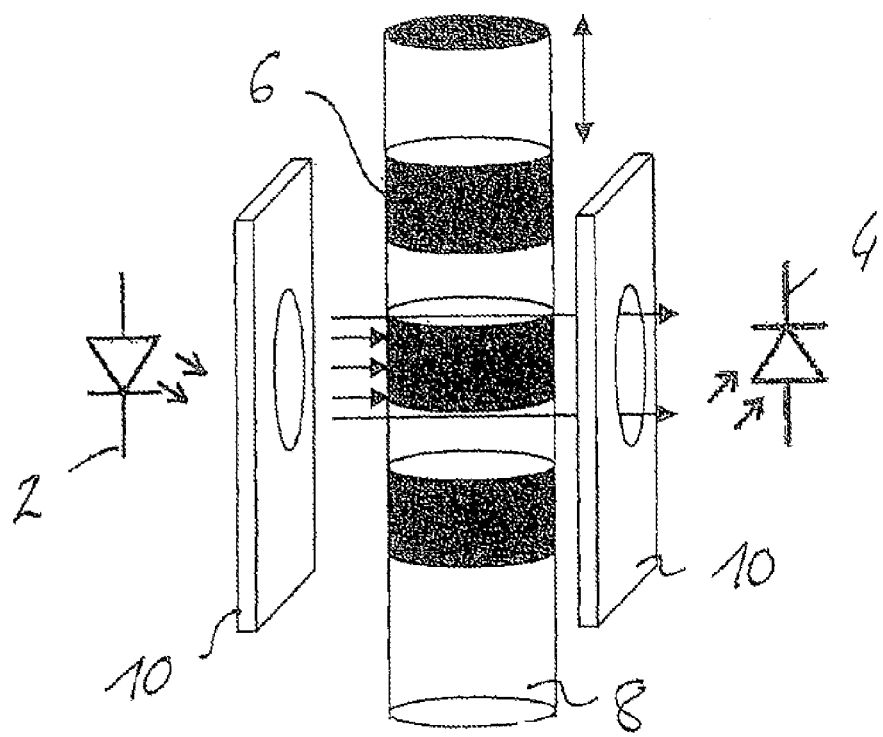
FIG. 5 shows a device for measuring a relative displacement.

FIG. 5 depicts a variant of the invention in which, instead of a twist, there is a longitudinal displacement of the main body 8 and hence also of the shadowing apparatuses 6 fixedly arranged thereon. Here too, the transmitter 2 and the sensor 4 lie opposite one another, wherein two stops 10 are arranged between the light source 2 and the sensor 4, between which stops the main body 8 with the shadowing apparatus 6 is arranged. The longitudinal displaceability is indicated by the double-headed arrow. The shadowing apparatuses 6 are arranged as rings at a distance from one another such that light-opaque regions and light-transmissive regions alternate. In the depicted example, the shadowing apparatus 6 arranged between the stops 10 is dimensioned in such a way that the stops 10 are not completely covered, and so some of the light rays from the transmitter 2 are incident on the sensor 4. If the main body 8 with the shadowing apparatus 6 is moved upward or downward, the light intensity increases by the proportion by which the non-shadowed area of the stops 10 is enlarged. If a plurality of sensors 4 are arranged in succession in the displacement direction, it is also possible, in addition to the displacement path, to determine the displacement direction from the phase shift.

Figure 6:
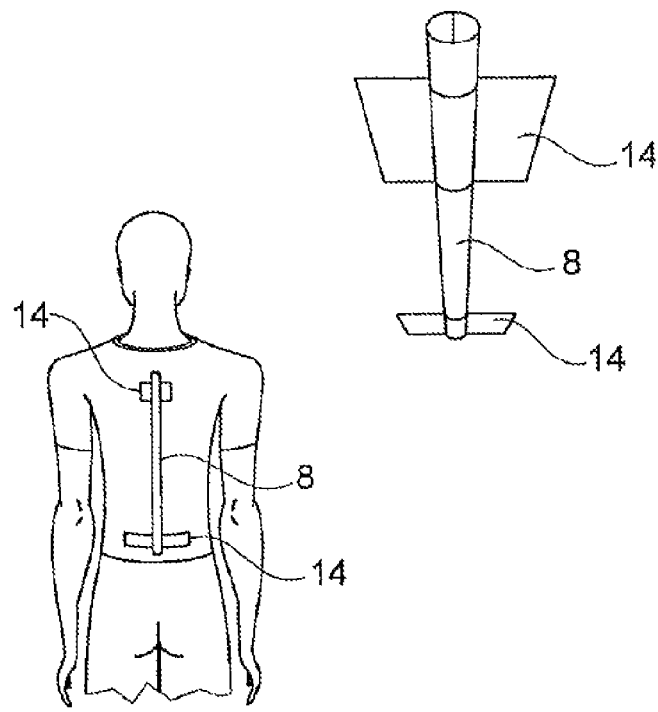
FIG. 6 shows an exemplary embodiment of the invention in the applied state.
Figure 7:
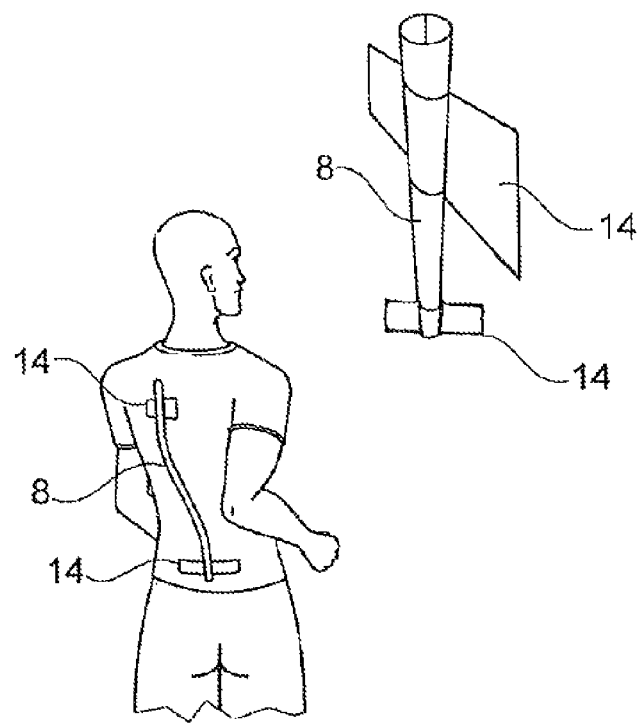

An applied exemplary embodiment is shown in FIGS. 6 and 7; FIG. 6 shows a person with a tightly fitting piece of clothing, on the surface of which a device for determining the spinal displacement is fastened. A main body 8 is fastened in the region of the lumbar vertebrae by means of an apparatus 14 for securing on the piece of clothing. By way of example, fastening is brought about by an adhesive tape such that there is a torsionally rigid fastening in the region of the lumbar vertebrae. A second apparatus 14 for securing on a body part is provided in the region of the upper thoracic vertebrae. In the upper illustration of FIG. 6, the alignment of both the main body 8 and the apparatuses 14 for securing on a body part is shown in a position in which the shoulders are substantially parallel to the pelvis. This alignment is elucidated by the vertical line at the upper end of the main body 8. Securing may also take place directly at the body on the skin.

FIG. 7 shows a twisted position of the spinal column of the person. Here, as seen from above, the upper body has twisted in the clockwise direction relative to the pelvis such that this has resulted in torsion of the spinal column in the clockwise direction. In the upper illustration of FIG. 7, it is possible to identify that, proceeding from the lower apparatus 14 for securing, the main body 8 has remained rigid, i.e. it has not twisted relative to the pelvis and the lower apparatus 14; however, the upper apparatus 14 for securing on the body part has twisted relative to the main body 8 to the same extent as the upper body of the person has twisted. If a sensor 4 is now arranged at the upper apparatus 14 for securing on a body part or a body area and, optionally, a light source 2 is also arranged on the opposite side, it is possible to determine the twist angle along the spinal column by means of the relative twist of the upper apparatus 14 and hence of the sensor as well. If a plurality of sensors and shadowing apparatuses are arranged along the longitudinal extent of the main body 8 and if light is fed in, for example, at a lower end face of the main body 8, one light source can be used for a highly resolved measurement of the individual twist angle along the spinal column using a plurality of sensors. Together with the shadowing apparatus 6, the main body 8 is arranged relatively displaceable to the upper apparatus 14; in the depicted exemplary embodiment, it is arranged in a twistable and longitudinally displaceable manner such that there can be a relative displacement in relation to the apparatus 14 for securing, even in the case of a forward and backward bending movement. The main body 8 is secured to the lower apparatus 14 in, in particular, a torsionally secure and non-displaceable manner.

A variant of the invention is shown in FIG. 8, in which light is fed from the transmitter 2 into the main body 8 on one side via the optical waveguide 12 and cast from said main body in the direction of a stop 10. Depending on the position of the shadowing apparatus 6 or the shadowing apparatuses, a greater or lesser light intensity will pass through a stop 10, which light intensity, in turn, is received by an optical waveguide 12 and conducted to the sensor 4. As a result, it is possible that both the transmitter 2 and the sensor 4 can be arranged at a distance from the point at which the relative displacement of the body areas in relation to one another occurs. Then, the main body 8 merely needs to be guided in a guide, for example an envelope, in which, or on which, the returning optical waveguide 12 to the photodiode is also arranged. As a result, the device can be kept very small; the transmitter 2, the sensor 4 and the evaluation apparatus 16 can then be attached to the body at a different location, which may optionally be less exposed, such that the whole device can be worn easily and inconspicuously. By way of example, the evaluation apparatus 16 can be arranged in a pocket which can be fastened to a piece of clothing.

The invention was described above on the basis of a transmitter 2 in the form of a light source. However, the functionality does not change when using other signal forms, i.e. electromagnetic waves, inductive energy transmission, magnetic fields and the like. Merely the sensors and the transmission media are adapted to the signal form.

The invention claimed is:

1. A device for determining relative displacements of body parts or body areas, comprising:
    a transmitter;
    a sensor assigned to the transmitter;
    a flexible conductor; and
    at least one shadowing apparatus positioned on or formed in the conductor, the at least one shadowing apparatus and conductor are configured to be secured to at least one body part or body area, are displaceable relative to at least one of the sensor and the transmitter, are arranged between the transmitter and the sensor, and are transmitted through, penetrated, transilluminated or illuminated by a signal from the transmitter in the direction of the sensor;
    wherein the transmitter is arranged next to the conductor and irradiates the conductor or feeds the signal in the longitudinal extent of the conductor into the conductor, the conductor transmits the signal from the transmitter to the sensor and through the at least one shadowing apparatus, and the sensor detects, based on the received signal, displacement of the at least one body part or body area relative to the at least one shadowing apparatus and conductor.

2. The device as claimed in claim 1, wherein the transmitter is embodied as a light source, magnet, emitter or transmitter emitting electromagnetic waves.

3. The device as claimed in claim 1, wherein the shadowing apparatus is arranged between the sensor and the transmitter and is directed to the sensor.

4. The device as claimed claim 1, wherein a plurality of shadowing apparatuses are arranged in succession in the displacement direction.

5. The device as claimed in claim 1, wherein the shadowing apparatus is embodied as a coating applied to the conductor as a polarization filter or as a region of the conductor with deviating transmittance or emission, deviating field line alignment or deviating magnetic flux.

6. The device as claimed in claim 5, wherein the conductor has a substantially round cross section.

7. The device as claimed in claim 5, wherein the conductor has an elongate embodiment and the transmitter is oriented perpendicular to the longitudinal extent of the conductor in a manner emitting in a direction toward the sensor.

8. The device as claimed in claim 1, wherein the shadowing apparatus is configured to be secured to the body part or body area in a torsion resistant manner at one end and freely rotatable at another end.

9. The device as claimed in claim 1, wherein at least one apparatus is assigned to the shadowing apparatus, on which at least one apparatus, which is configured to be secured on the body part or body area, at least one sensor is fastened and the shadowing apparatus is mounted in a manner displaceable relative to the sensor.

10. The device as claimed in claim 1, wherein the sensor is embodied for measuring an intensity in one or more frequency ranges.

11. The device as claimed in claim 1, wherein a plurality of sensors are arranged in succession in a longitudinal extent of the shadowing apparatus.

12. The device as claimed in claim 1, wherein an evaluation apparatus is assigned to the sensor.

13. A device for determining relative displacements of body parts or body areas, comprising:
 a transmitter;
 a sensor;
 a flexible conductor;
 at least one shadowing apparatus positioned on or formed in the conductor, the at least one shadowing apparatus and the conductor are configured to be secured to at least one body part or body area, are arranged between the transmitter and the sensor, are displaceable relative to at least one of the sensor and the transmitter, and are transmitted through, penetrated, transilluminated or illuminated by a signal of the transmitter in the direction of the sensor;
 wherein the transmitter is arranged next to the conductor and irradiates the conductor or feeds the signal in the longitudinal extent of the conductor into the conductor, the conductor transmits the signal from the transmitter to the sensor and through the at least one shadowing apparatus, and the sensor detects, based on the received signal, displacement of the at least one body part or body area relative to the at least one shadowing apparatus and conductor.

14. The device as claimed in claim 13, wherein the transmitter is embodied as at least one of a light source, a magnet, an emitter, or a transmitter emitting electromagnetic waves.

* * * * *